United States Patent [19]

Vollhardt et al.

[11] Patent Number: 4,734,264
[45] Date of Patent: Mar. 29, 1988

[54] CATALYTIC REACTOR FOR THE PRODUCTION OF METHANOL, AMMONIA, SYNTHESIS GAS AND HIGHER ALCOHOLS

[75] Inventors: Frohmut Vollhardt, Oberhausen; Hans-Dieter Krämer, Dinslaken, both of Fed. Rep. of Germany

[73] Assignee: MAN Gutehoffnungshautte GmbH, Fed. Rep. of Germany

[21] Appl. No.: 913,112

[22] Filed: Sep. 29, 1986

[30] Foreign Application Priority Data

Sep. 27, 1985 [DE] Fed. Rep. of Germany ....... 3534402
Feb. 22, 1986 [DE] Fed. Rep. of Germany ....... 3605792

[51] Int. Cl.$^4$ .............................. F28D 7/00; B01J 8/02
[52] U.S. Cl. .................................... 422/148; 422/200; 422/201; 423/360
[58] Field of Search ................. 422/148, 200, 201; 423/360; 165/173

[56] References Cited

U.S. PATENT DOCUMENTS 3,666,423  5/1972  Muenger ............................. 422/200
4,321,234  3/1982  Ohsaki et al. ....................... 422/200

Primary Examiner—Barry S. Richman
Assistant Examiner—William R. Johnson
Attorney, Agent, or Firm—McGlew and Tuttle

[57] ABSTRACT

A vertical reactor for catalytic exothermic and endothermic reactions, especially for the production of methanol, ammonia, synthesis gas and higher alcohols, with a jacket containing the catalyst bed and exchanger pipes which form a tube bundle running through the jacket parallel to its longitudinal axis, with a gas-permeable floor supporting the catalyst bed, as well as feed and discharge pipes for the cooling or heating medium running through the jacket lid and the jacket floor, said feed and discharge pipes, as well as feed and discharge pipes for the reaction gas, leading into horizontal distributing and collecting pipes wherein the upper and lower ends of the upright or essentially upright exchanger pipes of the tube bundle lead into horizontal supporting headers which are parallel to each other and arranged below and above the collecting and distributing pipes. The supporting headers are connected through intermediate ducts with the collecting or distributing pipes, which are arranged symmetrical to, or in the transverse center of, the support headers.

6 Claims, 7 Drawing Figures

CATALYTIC REACTOR FOR THE PRODUCTION OF METHANOL, AMMONIA, SYNTHESIS GAS AND HIGHER ALCOHOLS

BACKGROUND OF THE INVENTION

FIELD OF THE INVENTION

This invention relates, in general, to reaction vessel construction and in particular to a new and useful catalyst bed reactor for the catalytic exothermic and endothermic reaction to produce methanol, ammonia and synthesis gas and higher alcohols.

The invention relates particularly to a vertical reactor for the production of methanol, ammonia, synthesis gas and higher alcohols.

A reactor for catalytic reactions, especially for the production of methanol, is known from DE-OS No. 32 33 049. In it, a recirculation pipe jacket extends from an upper collecting ring to a lower distributing ring, the jacket's pipes being constructed as reinforced pipe sections in the upper and lower section of the reactor. Into these pipes lead so-called handle pipes, whose vertical sections form passageways in which the reactive mass is found, the reactive mass resting on a mesh in the lower region of the oven.

A reactor is known from DE-OS No. 33 34 775, defining the generic character of the primary claim, in which the replacement of the exchanger pipes connected with the supporting headers requires the separation of each exchange pipe from the supporting header, or the separation of the supporting header, with all of the exchanger pipes connected with it, from the upper and lower collecting and distributing pipe.

With regard to this known reactor, the proposition of the invention is to develop a less expensive and structurally simpler construction of the connection of the exchanger pipes with the supporting headers or collecting and distributing pipes, with which a good replaceability and repairability of the exchanger pipes and a more advantageous stationary connection of the exchanger pipes with the collecting and distributing pipes are provided.

SUMMARY OF THE INVENTION

In the reactor, according to the invention, the connecting sites of the exchanger pipes connected with the supporting headers are readily accessible from above or below, so that the replacement of several exchanger pipes is possible without all the exchanger pipes connected with a supporting header having to be loosened from the supporting headers, or the supporting headers from the distributing and collecting pipes.

A uniform static stress on the supporting headers is produced, in addition to a good accessibility of the connection sites of the exchanger pipes connected with them, if, in a round reactor, the collecting and distributing pipes are curved, and the intermediate ducts are connected with them by pairs symmetrical to the longitudinal center of the collecting and distributing pipes. A uniform space between the supporting headers and between the exchanger pipes connected with them ensures a good accessibility and repairability of the exchanger pipes and a uniform stress on the distributing and collecting pipes, as well as on the supporting headers.

In contrast to the prior art, the exchanger pipes of the reactor according to the invention exert only a vertical force on the parts supporting them and connected with them; the connecting sites of the exchanger pipes with the supporting headers are readily accessible from above or below, so that the replacement of several exchanger pipes is possible without the entire tube bundle having to be lifted out of the reactor. Also, the removal of the reactive mass from the interior of the reactor, which contains the exchanger pipes and is enclosed by a circular apron, can be readily undertaken.

Accordingly, it is an object of the invention to provide a reactor which comprises a vessel jacket including a central cylindrical portion with a top lid portion and a floor portion and with either or two curved collecting pipes arranged in the lid portion symmetrically on respective sides of the transverse central plane of the vessel jacket and a heat exchanger supporting header is arranged below and substantially transverse to collecting pipes and is connected by symmetrically arranged ducts to the collecting pipes, and wherein a plurality of heat exchanger tubes are arranged in vertical arrays below and connected to the upper supporting header connected at their lower ends to a lower supporting header which, in turn, is connected to symmetrically arranged distributor pipes connected to one or more inlets and wherein the catalyst's permeable floor is supported on bearing means below a lower heat exchanger supporting header for supporting a catalytic mass thereover between all of the heat exchanger pipes.

A further object of the invention is to provide a reactor which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

GENERAL DESCRIPTION OF THE PREFERRED EMBODIMENTS

Figure 2:
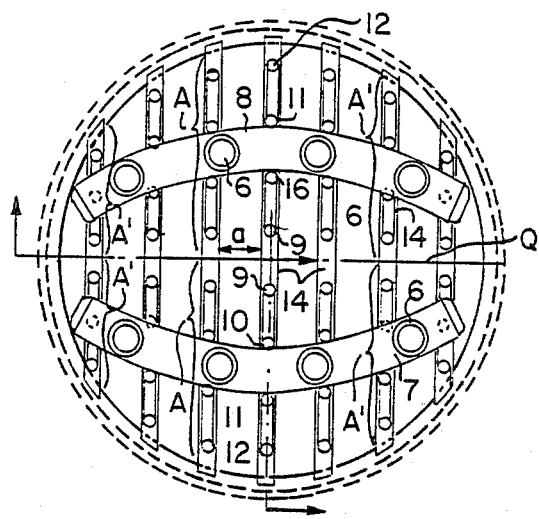
FIG. 2 is a horizontal cross-section through the upper portion of the reactor.

Referring to the drawings, in particular, the invention embodied therein comprises a reactor vessel generally designated 1 which includes a central cylindrical portion 2, a top lid portion 3, and a floor portion 4. In accordance with the invention, at least one curved collecting pipe, preferably two collecting pipes 7 and 8 are arranged in a lid portion symmetrically in respect to a central transverse plane Q (FIG. 2) above an array of vertically extending heat exchanger tubes 20 which are supported between an upper supporting header 14 and a lower supporting header 23. In addition, the gas permeable catalyst floor 27 is supported on bearing means 25 and carries a catalyst mass which extends between the heat exchanger tubes.

The reactor 1 has a cylindrical pressure jacket 2, to which are attached the lid 3 on the top and the similarly curved floor 4 on the bottom. Discharge pipes 6, for the heated medium, project through outlet ducts 5 into the interior of the reactor and there lead into two horizontal curved collecting pipes 7, 8. In the example shown, both pipes 7, 8 are arranged symmetrically to the transverse central plane Q of the reactor.

Intermediate ducts 9, 10, 11, 12 lead off from the curved collecting pipes 7, 8, the intermediate ducts lying, e.g. by fours, in a common plane and arranged by pairs symmetrical to the vertical central plane 13 of the pipes 7, 8, and leading into the supporting headers 14 at equal intervals. The supporting headers extend in a horizontal plane and are equidistantly parallel to each other.

Instead of the two collecting pipes 7, 8, it is possible to provide a single pipe in the transverse central plane Q, from which intermediate ducts, similar to the intermediate ducts 9–12, again run out leading into the supporting headers 14. In doing so, it must be taken into consideration that such a construction places high demands on the central collecting pipe, on which the entire bundle of heat exchanger pipes depends, as is described more precisely below. It is therefore advantageous to divide such a single pipe into the two curved supporting pipes 7, 8 represented in FIG. 2, which are then arranged symmetrical to the central plane Q and extend over the center of the pipe-halves of the pipes 6, i.e. extending centered above the halved pipe-lengths A,A' and A", for example FIG. 2. The central plane Q lies on the longitudinal axis of the jacket 2 and extends in a first transverse direction in the space defined by the jacket. The jacket also has a second transverse direction extending transversely to the first transverse direction.

In doing so, the intermediate ducts 9–12 lead into the collecting pipes 7, 8 in the lower and middle region.

Figure 1:
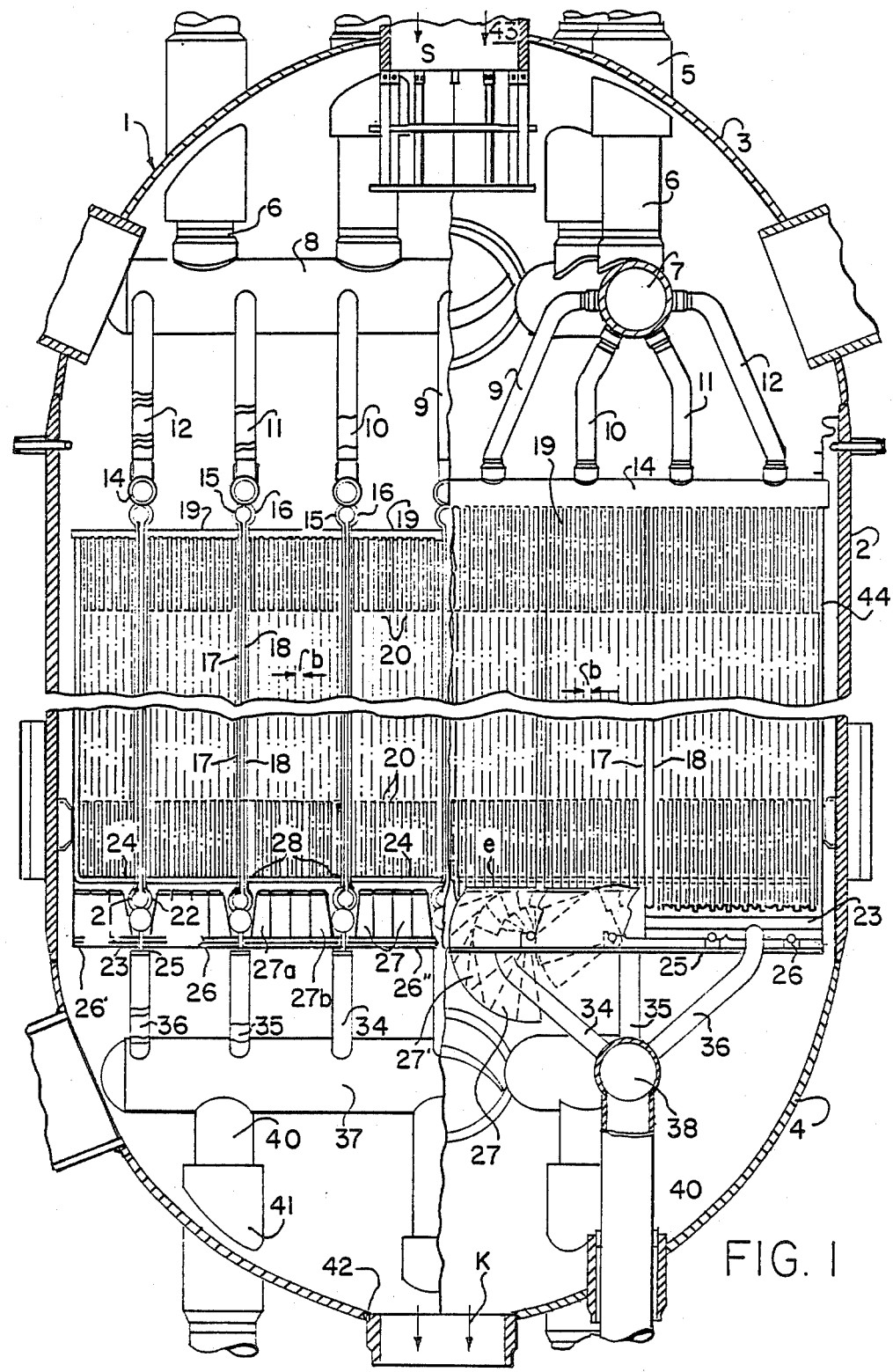
FIG. 1 is a combined vertical longitudinal sectional view through a reactor taken in two separate planes perpendicular to each other and constructed according to the invention for carrying out an exothermic reaction, e.g. for the production of methanol.
Figure 3:
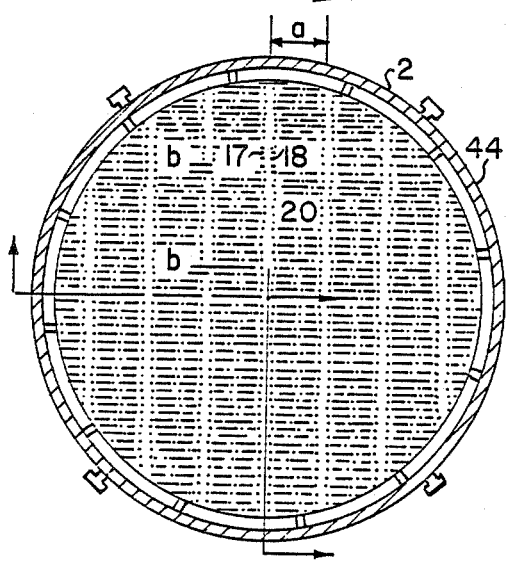
FIG. 3 is a cross-section through the middle.
Figure 4:
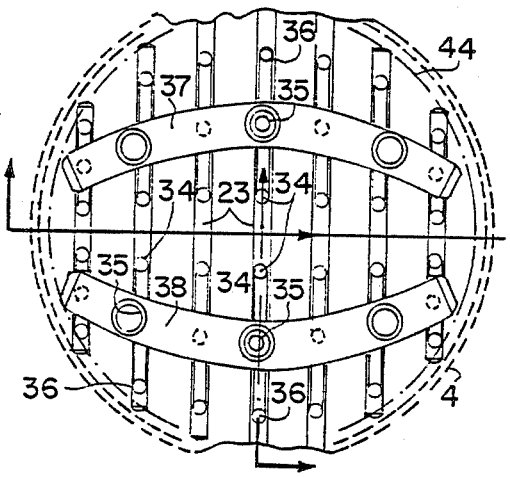
FIG. 4 is a horizontal cross-section through the lower section of the reactor.

The ends 15, 16 of the heat exchanger pipes 17, 18 lead into the lower region of the upper supporting headers 14. In doing so, the ends 15, 16 protrude outwards, as seen in FIG. 1, so that an advantageous connection of the pipes 17, 18 with the supporting headers 14 can result. The pipes 17, 18, to be designated as primary exchanger pipes, are arranged in the first transverse direction at intervals a, and in the second transverse direction, in the longitudinal direction of the supporting headers, they are connected with the supporting headers at intervals b. Upper secondary headers 19 extend just below the lateral protuberance, between the upper section of adjacent pipes 17, 18 at intervals a, on which upper headers depend additional exchanger pipes 20 at intervals b which run parallel to pipes 17, 18, so that, as seen in FIG. 3, a closed field is formed of parallel vertical exchanger pipes 17, 18 and 20 in the horizontal cross-section of the center section of the reactor, the exchanger pipes being equidistant from each other between which the catalyst mass is found.

The lower ends 21, 22 of the primary exchanger pipes 17, 18 lead into the lower supporting headers 23, which have the same arrangement as the upper supporting headers 14. The ends 21, 22 of the primary exchanger pipes 17, 18 are thus constructed in the same way as the upper ends 15, 16 of these pipes, as a lower secondary header 24 is also provided between the adjacent pipes 21, 22 at intervals a, the lower ends of the exchanger pipes 20 leading into said lower header. Said ends may also lead into the supporting headers 14, 23 through Y-pipes, instead of the lateral protuberances of the upper and lower ends of the pipes 17, 18.

Figure 6:
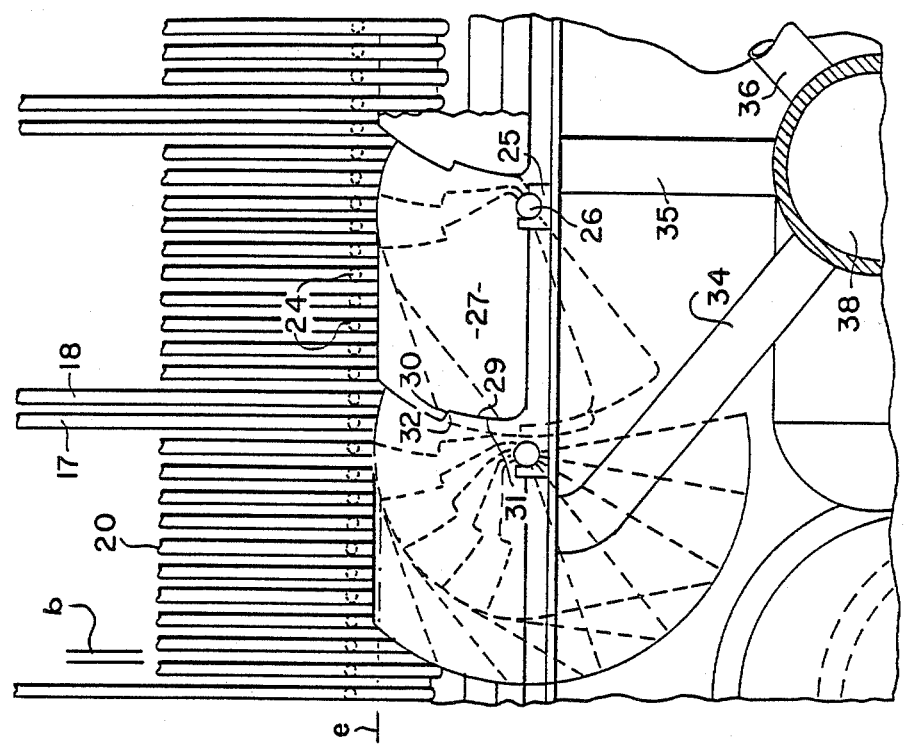
FIGS. 5 and 6 are vertical sectional views on a lager scale with respect to FIG. 1 of the lower region of the reactor showing the floor supporting the reactive mass and FIG. 7 is a view similar to FIGS. 5 and 6 showing a detail of this floor.
Figure 7:
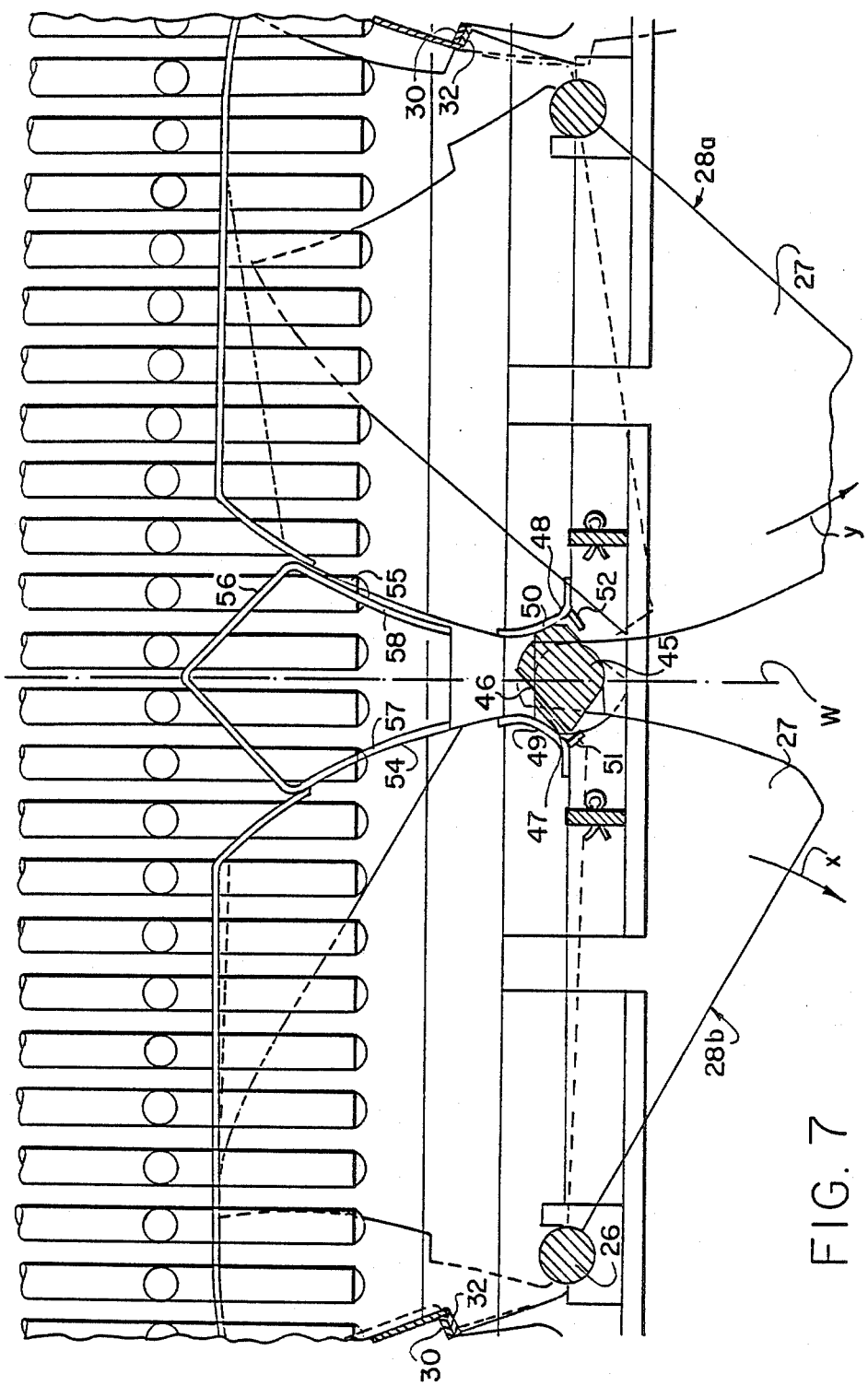

The lower supporting headers 23, running parallel to the upper supporting headers 14, have semi-circular bearings 25 underneath, which line up with each other in the transverse direction of the pipes 23 and several of them are arranged across the length of each supporting header 23. Between adjacent, lining up with each other bearings 25 are arranged shafts 26 to which elements 27 are fastened next to each other, groups of the elements 27, by fours in the represented example, forming a section 28 of the catalyst floor, this section lying in a plane e when in the folded-upward operation position 27 (FIGS. 6 and 7, in the inked-in line). The elements 27 of the sections 28 forming the catalyst floor are gas-permeable. The outer elements 27a, 27b of a section 28 lie, in the folded-upward position of the sections, next to the pipes 23. The catalyst mass rests on the sections 28 which, viewed from the top, form a square with a side length somewhat smaller than the interval a.

Figure 5:
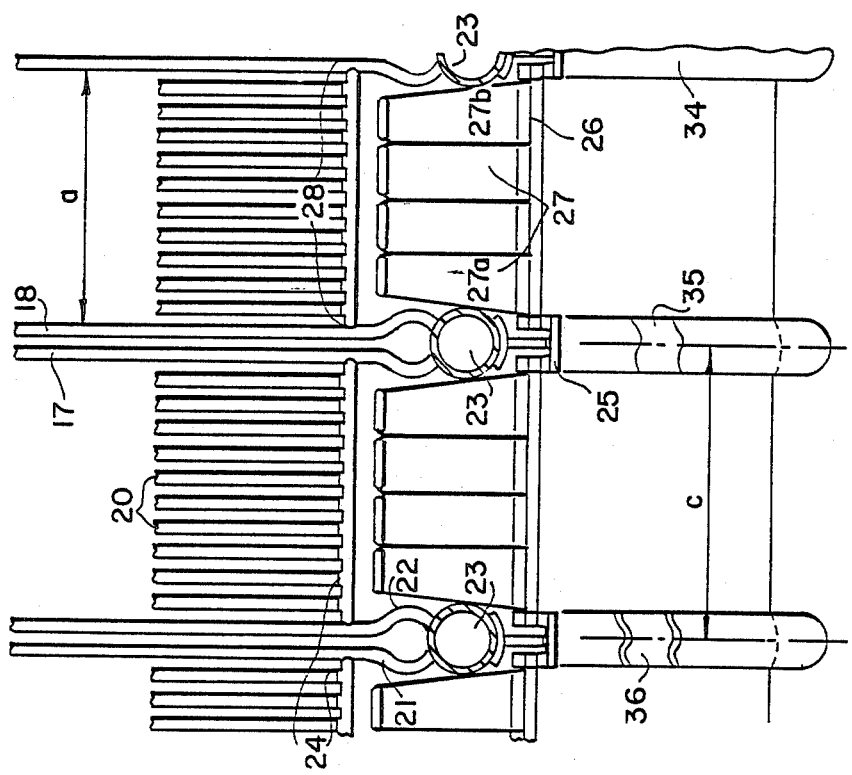

The back side 29 adjacent to the shaft 26 has an indent 30, while the front side 31 of each element 27, facing away from the shaft 26, has a lug-like projection 32 (see FIG. 6). The construction and arrangement of the projection 32 and of the indent 30 is set up so that, in the folded-upward operating position of the sections 28, the sections hold each other in a position by the meshing of adjacent indents and projections, the last section of each row (in FIG. 1, the one on the left-hand edge of the drawing) to be conceived as fixed. If this one is disconnected and swings downwards, first the projection and indent of the section next to this first section fall out of engagement, so that it swings downwards between the pipes 23 and all the remaining sections, whose shafts line up with each other, do the same, as e.g. the shafts 26', 26", 26"', etc. in FIG. 5.

The lower supporting headers 23 are connected with two distributing pipes 37, 38 through intermediate ducts 34, 35, 36, the distributing pipes being arranged symmetrical to the transverse central plane Q and leading into half of all the intermediate ducts 34, 35, 36. The distributing pipes are connected with the feed pipes 40, which extend through an inlet duct 41 in the floor 4 of the reactor. The floor shows the effluent pipe 42 for the medium, flowing in the direction of arrow K, which enters the reactor through the entry pipe 43 of the lid 3 in the direction of arrow S.

The exchanger pipe bundle of pipes 17–20 is enclosed by an apron 44.

FIG. 7 represents the middle section of the lower region of the reactor containing the catalyst floor, as it may be advantageously constructed by using the previously described hinged floor sections 28. A continuous horizontal shaft 45 extends parallel to the individual shafts 26, in the vertical central plane of the reactor W, across the entire cross-section of the reactor, this shaft being rotatable by means not represented and bearing supports 46, at least the distance of the individual floor sections from each other, which are immovably connected with the shaft 45. These supports have two supporting surfaces 47, 48 symmetrical to the perpendicular central axis of the shaft 45 and to the central plane of the reactor W, on which are braced supporting surfaces 49, 50 of the facing elements 27 of the middle floor sections 28, the arrangement of the sections being set up so that they will tilt in opposite directions on each side of plane W. (Cf. arrox x, y in FIG. 7). The shaft 45 represents a sort of balance arm with the supporting surfaces. By rotating the shaft 45 counter-clockwise, for example, the right-hand section 28a first becomes free also. If the floor sections 28 jam, e.g. as a result of the catalyst mass burning, the appropriate edges of the supports 46 push against attachments or tappets 51, 52 on the lower end of the supporting surfaces 49, 50 of elements 27 or of the sections 28. At times, a rotation of shaft 45° by 90° is thus necessary in order to open the next section 28.

The area 53 between the pivoted front sides 54, 55 of the sections 28a, 28b next to each other in the center of the reactor is covered by roof-like part 56 whose side pieces 56, 58 are fitted to the front sides 54, 55 of the elements 27.

In order to carry out an endothermic reaction, the exchanger pipes 17, 18 are filled with a heating medium; the collecting and distributing pipes 6, 7 or 37, 38 are connected with the appropriate feed and discharge pipes.

While specific embodiments of the invention have been shown and described in detail to illustrate the application of the principles of the invention, it will be understood that the invention may be embodied otherwise without departing from such principles.

What is claimed is:

1. A vertical reactor for catalytic exothermic and endothermic reactions, especially for the production of methanol, ammonia, sythesis gas, and higher alcohols, comprising:
   a jacket (2) defining a space and having a vertical longitudinal direction, said jacket having a tranverse central plane(Q) lying on said longitudinal axis and extending in a first transverse direction, and a second transverse direction extending transversely to said first transverse direction;
   a lid (3) connected to a top end of said jacket and closing a top end of said space;
   a floor (4) connected to a bottom end of said jacket and closing a bottom end of said space;
   an effluent pipe (42) connected to said floor and communicating with said space for the effluent of gases that have reacted in said space;
   an entry pipe (43) connected to said lid and communicating with said space for the entry of gases to react in said space;
   a plurality of discharge pipes (6) connected to and supported by said lid, said discharge pipes extending into said space;
   a plurality of feed pipes (40) connected to said floor, said feed pipes extending into said space;
   two spaced apart curved collecting pipes (7, 8) each connected to at least one of said pipes and positioned on opposite sides of said transverse central plane, said collecting extending substanially in said second transverse direction;
   two distributing pipes (37, 38) each connected to at least one of said feed pipes;
   a plurality of upper supporting headers (14) extending below said collecting pipes in said second transverse direction and being spaced from each other in said first transverse direction;
   a plurality of upper intermediate ducts (9, 10, 11, 12) connected between said upper supporting headers and said collecting pipes with each upper supporting header being connected to one of said collecting pipes through a plurality of said upper intermediate ducts;
   a plurality of lower supporting headers (23) extending in said second transverse direction and being spaced from each other in said first transverse direction;
   a plurality of lower intermediate ducts (34, 35, 36) connected between said distributing pipes and said lower supporting headers, each lower supporting header being connected to one of said distributing pipes by plurality of intermediate ducts;
   said upper supporting headers being spaced above said lower supporting headers in said space;
   a plurality of primary heat exchanger pipes (17, 18) connected between said upper and lower supporting headers, said primary heat exchanger pipes extending parallel to said longitudinal direction and being spaced from each other in said first and second tranverse directions, each of said upper supporting headers being connected to one of said lower supporting headers by a plurality of primary heat exchanger pipes which are spaced from each other in said second transverse direction;
   a plurality of upper secondary headers (19) each connected between a pair of primary heat exchanger pipes which are connected to an adjacent pair of upper supporting pipes;
   a plurality of lower secondary headers (24) each connected between a pair of primary heat exchanger pipes which are connected to an adjacent pair of lower supporting headers;
   said upper secondary headers being adjacent upper ends of said primary heat exchanger pipes and said lower secondary headers being adjacent lower ends of said primary heat exchanger pipes;
   a plurality of secondary heat exchanger pipes (20) connected between said upper and lower secondary headers with each upper secondary header being connected to one of said lower secondary headers by plurality of said secondary heat exchanger pipes;
   said primary and secondary heat exchanger pipes being spaced apart from each other in said first and second transverse directions to form a regular grid of heat exchanger pipes all extending parallel to said longitudinal axis; and
   catalyst floor means (27) for defining a catalyst floor near and above said supporting headers, said catalyst floor being spaced above said flow of said jacket for supporting a catalyst bed above said catalyst floor through which said primary and secondary heat exchanger pipes extend for an even distribution of heat exchange through said catalyst bed by said regularly spaced heat exchanger pipes;
   said heat exchanger pipes being supported between said discharge and said feed pipes for permitting removal of said grid of heat exchanger pipes as a unit from said jacket.

2. A reactor according to claim 1 wherein said primary heat exchanger pipes are connected in pairs between vertically spaced pairs of upper and lower supporting headers, each primary heat exchanger pipe having a lateral protuberance bending laterally in said first transverse direction, each protuberance being positioned between a secondary header and an adjacent supporting header.

3. A reactor according to claim 2 wherein each upper secondary header is positioned immediately below protuberances of adjacent primary heat exchanger pipes, and each lower secondary header is positioned immediately above protuberances of adjacent primary head exchanger pipes.

4. A reactor according to claim 1 wherein said jacket is cylindrical, said lid and floor are both hemispherical, said collecting pipes being in said lid and said distributing pipes being in said floor, said distributing pipes being curved and being positioned on opposite sides of said transverse central plane.

5. A reactor according to claim 4 wherein said intermediate ducts are connected to said supporting headers at equally spaced locations along each supporting header in said second transverse direction.

6. A reactor according to claim 5 including a plurality of outlet ducts fixed to said lid each supporting one of said discharge pipes and a plurality of inlet ducts fixed to said floor each supporting one of said feed pipes for supporting said heat exchanger tubes between said lid and floor.

* * * * *

UNITED STATES PATENT OFFICE
CERTIFICATE OF CORRECTION

Patent No. 4,734,264          Dated Mar. 29, 1988

Inventor(s) Frohmut Vollhardt, Hans-Dieter Krämer

It is certified that error appears in the above-identified patent and that said Letters Patent are hereby corrected as shown below:

ON THE TITLE PAGE:

Assignee's name should be shown as:

MAN Gutehoffnungshütte GmbH
        Fed. Rep. of Germany

Signed and Sealed this

Fourteenth Day of March, 1989

*Attest:*

DONALD J. QUIGG

*Attesting Officer*      *Commissioner of Patents and Trademarks*